United States Patent [19]

Macaluso, Sr.

[11] 3,950,439

[45] Apr. 13, 1976

[54] PRODUCTION OF LINEAR PRIMARY ALCOHOLS

[75] Inventor: Anthony Macaluso, Sr., Port Arthur, Tex.

[73] Assignee: Texaco Inc., New York, N.Y.

[22] Filed: July 12, 1974

[21] Appl. No.: 488,130

Related U.S. Application Data

[63] Continuation-in-part of Ser. No. 271,310, July 13, 1972, abandoned.

[52] U.S. Cl............... 260/632 HF; 260/617 R
[51] Int. Cl.$^2$........................... C07C 29/16
[58] Field of Search............. 260/632 HF

[56] References Cited
UNITED STATES PATENTS

| | | | |
|---|---|---|---|
| 2,877,274 | 3/1959 | Kramis | 260/632 A |
| 3,278,612 | 10/1966 | Greene | 260/632 HF |
| 3,351,666 | 11/1967 | Mertzweiller et al. | 260/632 HF |
| 3,418,351 | 12/1968 | Greene et al. | 260/632 HF |

FOREIGN PATENTS OR APPLICATIONS

| | | | |
|---|---|---|---|
| 672,635 | 5/1952 | United Kingdom | 260/632 HF |

OTHER PUBLICATIONS

Hatch, *Higher Oxo Alcohols*, 1957, pp. 5 and 6.

*Primary Examiner*—Joseph E. Evans
*Attorney, Agent, or Firm*—T. H. Whaley; C. G. Ries; Henry W. Archer

[57] ABSTRACT

A hydroformylation process for increasing the yield of straight chain unsubstituted primary alcohols from predominantly terminal olefins by contacting the olefins with carbon monoxide and hydrogen in the presence of a cobalt catalyst is characterized by the incorporation of aqueous base in a base to cobalt molar ratio of about 10:1 to 20:1 in the reaction mixture before or after heating the same to reaction temperature. The base introduced in the oxo reactor while hydroformylation is occurring continuously converts byproducts acetals and esters to the corresponding primary alcohols, thereby considerably increasing the yield thereof.

9 Claims, No Drawings

PRODUCTION OF LINEAR PRIMARY ALCOHOLS

CROSS REFERENCE TO CO-PENDING APPLICATION

This application is a continuation-in-part of coassigned patent application Ser. No. 271,310 filed July 13, 1972 and now abandoned.

BACKGROUND OF THE INVENTION

Field of the Invention

This invention relates to a process for making primary alcohols characterized by the use of base to suppress formation of carbonyl reaction by-products to increase the yield of linear primary alcohols.

These alcohols have utility as solvents and as intermediates in plasticizer and lubricant manufacturing. Some of the higher alcohols are used as surface active agent intermediates but their biodegradability is inversely proportional to the amount of branched isomer present in the final alcohol product.

DESCRIPTION OF THE PRIOR ART

In the past, linear primary alcohols have been prepared by processes based on the oxo or hydroformylation reaction by treating olefinic compounds with carbon monoxide and hydrogen at elevated temperatures and pressure and in the presence of various cobalt-based catalyst. A characteristic of such processes is that the percentage of linear isomers in the final product decreases as the chain length of the olefin increases. This is disadvantageous where biodegradability of the product is desired.

The art in this field is already aware, inter alia, of U.S. Pat. Nos. 3,420,898; 3,278,612; 3,418,351 and of British Pat. No. 672,635 of 1952. U.S. Pat. No. 3,278,612 describes a hydroformylation process for $C_2$ to $C_{12}$ olefins to produce alcohols without the formation of contaminating high-boiling materials such as acetals. The result of the process is an alcohol having $2n + 2$ carbon atmos per molecule. In the process of U.S. Pat. No. 3,278,612 a preformed cobalt carbonyl/butylphosphine catalyst complex is added to the reaction mixture together with synthesis gas and the resulting mass is heated to reaction temperature. Apparently, the ratio of base to catalyst given in the patent is not sufficient to increase the amount of straight chain isomer produced.

It is therefore the main object of this invention to provide an improved hydroformylation process which yields alcohols containing more linear isomer and less organic carbonyl compounds as by-products than alcohols prepared by prior art processes.

In accordance with the invention, terminal olefins, internal olefins having n carbons to the molecule where n has a value of 11 to 20 with or without a solvent, and/or olefin-paraffin mixtures are contacted with a cobalt carbonyl, phosphine catalyst complex prepared in situ and a caustic solution. The reaction mixture is initially pressured with carbon monoxide and hydrogen, preferably in the form of synthesis gas, and heated to 200°F to 900°F under pressures of 1000 to 3500 psig, preferably from 2500 to 3000 psig, and reaction times from 1 to 20 hours and preferably from 3 to 10 hours. The preferred practise is to add first a minor part of synthesis gas, heat to reaction temperature and then add the major part of the gas. The product is predominantly a straight chain alcohol having $n + 1$ carbon atoms to the molecule.

The caustic solution can be an aqueous basic solution, organic solution of an alkali metal hydroxide, and/or a metal salt of an organic acid. The preferred solution is 20% aqueous sodium hydroxide. This basic solution can be added to the reaction zone along with the catalyst and olefin charge prior to heating to reaction temperature or after reaction temperature has been reached. The molar ratio of base to cobalt is about 10:1 to 20:1.

The ratio of base to olefin charge may vary widely within the scope of the invention. A base to olefin molar ratio may vary from about 0.05:1 to 10:1, preferably from 0.1:1 to 3:1 and more preferably from 0.1:1 to 1:1.

The ratio of hydrogen to carbon monoxide also may vary widely within the scope of the invention. In general, the mole ratio of hydrogen to carbon monoxide comprises those within the range of 2 to 10 in order to minimize the formation of carbonyl compounds.

The cobalt source can be dicobalt octacarbonyl, the cobalt salt of an organic acid such as cobalt acetate, cobalt adsorbed on a support or cobalt itself. Other metal or metal complexes capable of catalyzing the oxo reaction may be used. The Group VA organo-ligand can be any organophosphine, preferably tri-n-butylphosphine, phosphite, phosphate, phosphonate, or other ligands which form a complex with the carbonyl. While some of these ligands may be basic in nature they do not serve the same purpose as the above caustic solution.

The ratio of catalyst to reactants is not critical. Thus, ratios of catalyst to olefin between about 1:1000 to about 10:1 have been found satisfactory.

The process of the invention is generally applicable to the hydroformylation of any aliphatic or cyclo-aliphatic compounds having at least one ethylenic double bond. The invention is used to particular advantage in the hydroformylation of olefins having from 11 to 14 carbons to produce predominantly linear alkanols having one more carbon atoms than the starting olefin. As pointed out above, prior art techniques have generally resulted in a rather poor yield of linear product.

A comparison of the linear: branched alcohol ratio obtained from runs wherein aqueous sodium hydroxide was added to the reaction mixture to a run wherein aqueous caustic was not added is presented in the following examples:

EXAMPLE I

Cobalt acetate tetrahydrate (7.6 g., 0.03 mols of cobalt), tri-n-butylphosphine (6.2 g., 0.03 moles), 20% aqueous sodium hydroxide (50 ml.) and $C_{11}$–$C_{14}$ alpha olefins (172.8 g., 1.0 mol) were added to a 1000-ml. stainless steel autoclave and the reactor was flushed with synethesis gas (hydrogen:carbon monoxide molar ratio of 2), pressured to 500 psig and heated to reaction temperature (350°F.). Once reaction temperature was reached, the reactor was pressured with synthesis gas (hydrogen:carbon monoxide molar ratio of 2) to 3000 psig. The reaction was allowed to continue until no further up-take of the synthesis gas was observed. At the end of this time (4 hours), the autoclave was cooled, vented and emptied. The crude reaction mixture was water-washed several times and the organic layer was collected. The organic layer was decobalted with several successive portions of a 10 percent aqueous acetic acid solution. The decobalted reaction effluent was then vacuum fractionated to remove unreacted olefins and mixed paraffins. The product alcohols were then taken overhead in 90 mol % selectivity and contained 83% of the linear isomer. Olefin conversion was calculated as 67 wt. %.

EXAMPLE II

Cobalt acetate tetrahydrate (7.6 g., 0.03 mols of cobalt), tri-n-butylphosphine (6.2 g., 0.03 mols), 50% aqueous sodium hydroxide (25 ml.) and the $C_{11}$-$C_{14}$ alpha olefins (172.8 g., 1.0 mol) were added to a 1000-ml. stainless steel autoclave and the reactor was flushed with synthesis gas (hydrogen : carbon monoxide molar ratio of 2), pressured to 500 psig and heated to reaction temperature (350°F.). Once reaction temperature was reached, the reactor was pressured with the synthesis gas (hydrogen : carbon monoxide molar ratio of 2) to 3000 psig. The reaction was allowed to continue until no further up-take of the synthesis gas was observed. At the end of this time (4 hours), the autoclave was cooled, vented and emptied. The crude reaction mixture was water-washed several times and the organic layer was collected. The organic layer was decobalted with several successive portions of a 10 percent aqueous acetic acid solution. The decobalted reaction effluent was then vacuum fractionated to remove unreacted olefins and mixed paraffins. The product alcohols were then taken overhead in 92 mol % selectivity and contained 83% of the linear isomer. Olefin conversion was calculated as 59 wt. %.

EXAMPLE III

Cobalt acetate tetrahydrate (7.6 g., 0.03 mols of cobalt), tri-n-butylphosphine (6.2 g., 0.03 mols) and $C_{11}$-$C_{14}$ alpha olefins (172.8 g., 1.0 mol) were added to a 1000-ml. stainless steel autoclave and the reactor was flushed with synthesis gas (hydrogen : carbon monoxide molar ratio of 2), pressured to 500 psig and heated to the reaction temperature (350°F). A reaction pressure of 3000 psig was maintained by periodically adding synthesis gas to the reaction mixture. The reaction was allowed to continue until no further up-take of the synthesis gas was observed. At the end of this time (65 minutes), the autoclave was cooled, vented and emptied. The crude reaction effluent was decobalted with several successive portions of a 10 percent aqueous acetic acid solution. The decobalted reaction effluent was then vacuum fractionated to remove light minerals. The produce alcohols were then taken overhead in 93 mol % selectivity and contained 69% of the linear isomer. Olefin conversion was calculated as 62 wt. %.

The advance in the art represented by the present process is emphasized by the foregoing examples where carrying out the oxo reaction in the presence of base with $C_{11}$-$C_{14}$ alpha olefins gave product alcohols containing 83% of the linear isomer. By contrast, operating without base but keeping all other reaction conditions, the same gave product alcohols containing only 69% of linear isomer. Also noteworthy is the ratio of absorbancies in the infrared carbonyl region which was found to be as follows:

|  | Aldehyde Carbonyl | Ester Carbonyl |
|---|---|---|
| Without aqueous NaOH | 3.2:1.0 | 13.5:1.0 |
| With aqueous NaOH |  |  |

What is claimed is:

1. A hydroformylation process for the conversion of unsubstituted olefinic hydrocarbons consisting of predominantly straight chain terminal olefins having n carbon atoms per molecule to predominantly straight chain linear alcohols having $n+1$ carbon atoms to the molecule, n being from 11 to 20, inclusive, comprising reacting said hydrocarbons with carbon monoxide and hydrogen at a temperature of from about 200°F to about 5000°F. and a pressure of from about 1000 to 3500 psig for a reaction time of from about 1 to 20 hours in the presence of a cobalt tri-alkylphosphine oxo catalyst prepared in situ and of an aqueous base selected from the group of alkali metal hydroxides, and alkali metal salts of organic acids, the molar ratio of base to olefinic hydrocarbons, being from about 0.05 to 1 to 10 to 1, and the molar ratio of base to cobalt being from about 10:1 to 20:1.

2. The process of claim 1 wherein said aqueous base is sodium hydroxide.

3. The process of claim 1 wherein said reaction temperature ranges from 340°F. to 400°F.

4. The process of claim 1 wherein the reaction pressure ranges from 2500 to 3000 psig.

5. The process of claim 1 wherein said hydrogen and said carbon monoxide are present in synthesis gas, a minor part of said gas being added, followed by heating to reaction temperature followed by introduction of the major part of the gas.

6. The process of claim 1 wherein the catalyst is cobalt in complex combination with carbon monoxide and a tri-alkyl phosphine.

7. The process of claim 1 wherein the ratio of hydrogen to carbon monoxide ranges from 2:1 to 10:1 and the ratio of base of olefinic hydrocarbons is from about 0.1 to 1:1.

8. The process of claim 1 wherein said base is introduced with said catalyst and said olefins prior to heating to reaction temperature.

9. The process of claim 1 wherein said base is introduced after said catalyst and said olefins are heated to reaction temperature.

* * * * *